(12) United States Patent
Blau

(10) Patent No.: US 6,790,990 B2
(45) Date of Patent: Sep. 14, 2004

(54) METHOD FOR PREPARING FLUOROSULFONYL IMIDE MONOMER

(75) Inventor: Hanne Anna Katherina Blau, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 740 days.

(21) Appl. No.: 10/168,278

(22) PCT Filed: Dec. 18, 2000

(86) PCT No.: PCT/US00/34074

§ 371 (c)(1),
(2), (4) Date: Jun. 14, 2002

(87) PCT Pub. No.: WO01/47872

PCT Pub. Date: Jul. 5, 2001

(65) Prior Publication Data

US 2003/0013915 A1 Jan. 16, 2003

Related U.S. Application Data

(60) Provisional application No. 60/167,048, filed on Dec. 23, 1999.

(51) Int. Cl.$^7$ .................... C07C 303/36; C07C 303/40
(52) U.S. Cl. ........................................... 564/82
(58) Field of Search ........................................... 564/82

(56) References Cited

U.S. PATENT DOCUMENTS

| 3,301,893 A | 1/1967 | Putnam et al. |
| 3,560,568 A | 2/1971 | Resnick |
| 4,940,525 A | 7/1990 | Ezzell et al. |
| 5,463,005 A | 10/1995 | Desmarteau |

*Primary Examiner*—Peter O'Sullivan

(57) ABSTRACT

Disclosed is a method for the preparation of a fluorosulfonyl imide monomer of the structure represented by formula (IV), wherein X is F or perfluoroalkyl having 1–4 carbons optionally substituted by ether oxygen, M is an alkali or alkaline earth metal when y is respectively 1 or 2, R is aryl, fluoro-aryl, or $XCF_2$-where X is H, halogen, fluorinated or

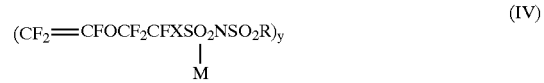

$$(CF_2\!\!=\!\!CFOCF_2CFXSO_2NSO_2R)_y \atop M \qquad\qquad\qquad\text{(IV)}$$

non-fluorinated linear or cyclic alkyl having 1–10 carbons, optionally substituted by one or more ether oxygens. Such monomers are useful for forming ionomers useful in electrochemical applications such as batteries, fuel cells, electrolysis cells, ion exchange membranes, sensors, electrochemical capacitors, strong acid catalysts, and modified electrodes.

23 Claims, No Drawings

METHOD FOR PREPARING FLUOROSULFONYL IMIDE MONOMER

This application is a 371 of PCT/US00/34074 filed Dec. 18, 2000 which claims to benefit of Ser. No. 60/167,048, filed Dec. 23, 1999.

FIELD OF THE INVENTION

The present invention is directed to a method for the preparation of a fluorosulfonyl imide monomer useful for forming ionomers. Such ionomers are useful in electrochemical applications such as batteries, fuel cells, electrolysis cells, ion exchange membranes, sensors, electrochemical capacitors, strong acid catalysts, and modified electrodes.

BACKGROUND OF THE INVENTION

Monomers represented by the formula $$CF_2=CFOCF_2CF_2SO_2F \qquad (I)$$

are employed by Ezzell et al., U.S. Pat. No. 4,940,525 to form copolymers with TFE followed by hydrolysis to the ionomer form. Ionomers of the type disclosed by Ezzell are suitable for a variety of electrochemical applications including the chloralkali process.

Putnam et al., U.S. Pat. No. 3,301,893, or in the alternative Resnick, U.S. Pat. No. 3,560,568, discloses a process for preparing $CF_2=CFOCF_2CF_2SO_2F$ by pyrolysis of $FSO_2CF_2CF_2OCFCF_3COONa$. Resnick, op.cit., forms a cyclic sulfone of the formula

(II)

by pyrolyzing the $FSO_2CF_2CF_2OCFCF_3C(O)F$ of Putnam in the presence of $Na_2CO_3$. Resnick then reacts the cyclic sulfone (II) with sodium methoxide to form $CF_2=CFOCF_2CF_2SO_3Na$ which is then converted through a series of steps to the monomer (I) followed by copolymerization with TFE and subsequent hydrolysis to the ionomer form.

Putnam discloses the generalized reaction scheme

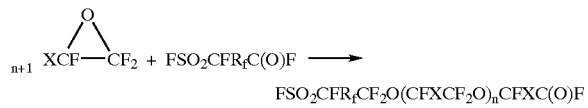

where X is $CF_3$- or F, and $R_f$ is F or perfluoroalkyl.

Xue, Ph.D. Thesis, Clemson University, 1996, shows that a composition containing $CF_3SO_2NNa_2$ when reacted with the cyclic sulfone (II), provides a 4% yield of $CF_2=CFOCF_2CF_2SO_2N(Na)SO_2CF_3$ (III) amidst a much larger yield of saturated species. Xue provides no method for achieving a higher yield of (III). There is no teaching in Xue in regard to the concentration of $CF_3SO_2NNa_2$ in the reaction mixture, nor as to the relationship between yield of (III) and the concentration of the $CF_3SO_2NNa_2$.

DesMarteau, U.S. Pat. No. 5,463,005, discloses the copolymer of (III) with tetrafluoroethylene to form an ionomer. Feiring et al., WO9945048(A1), disclose the copolymer of (III) with vinylidene fluoride to form a lithium ionomer.

SUMMARY OF THE INVENTION

The present invention is a process for forming, at a yield greater than 50 mol-%, a monomeric composition represented by the formula $$(CF_2=CFOCF_2CFXSO_2N(M)SO_2R_y \qquad (IV)$$

wherein X is F or perfluoroalkyl having 1–4 carbons optionally substituted by ether oxygen, M is an alkali or alkaline earth metal when y is respectively 1 or 2, R is aryl, fluoro-aryl, or $XCF_2$- where X is H, halogen, fluorinated or non-fluorinated linear alkyl having 1–10 carbons or cyclic alkyl having 3–10 carbons, optionally substituted by one or more ether oxygens;

the process comprising:
contacting in an inert atmosphere a cyclic sulfone represented by the structure

(II)

wherein X is F or perfluoroalkyl having 1–4 carbons optionally substituted by ether oxygen with a composition sulfonyl amide salts of which said salts at least 50 mol-% are sulfonyl amide salts represented by the formula $$(RSO_2NM_b)_{3-b}M'_c \qquad (V)$$

wherein R is aryl, fluoro-aryl, or $XCF_2$- where X is H, halogen, fluorinated or non-fluorinated linear alkyl radicals having 1–10
where R is aryl, fluoro-aryl, or $XCF_2$- where X is H, halogen, fluorinated or non-fluorinated linear alkyl radicals having 1–10 carbons or cyclic alkyl radicals having 3–10 carbons, optionally substituted by one or more ether oxygens, M' is an alkaline earth metal, b=1 or 2, c=0 or 1, M is alkaline earth or alkali metal when b is 1 or 2 respectively and c=0, and M is alkali metal when b=1 and c=1, with the proviso that c≠1 when b=2, thereby forming a ring-opening reaction mixture; reacting said ring-opening reaction mixture at a temperature in the range of 0 to 67° C.

As used herein, the term "reacting" is intended to mean allowing at least two components in a reaction mixture to react to form at least one product. "Reacting" may optionally include stirring and/or heating or cooling.

DETAILED DESCRIPTION

The present invention provides a process for converting a cyclic sulfone (II) into a monomer (IV) under conditions leading to a yield of greater than 50 mol-%, preferably greater than 90 mol-%, most preferably greater than 95 mol-% as compared to a yield of only 4% according to the art.

While Xue, op.cit., shows that a composition containing $CF_3SO_2NNa_2$ when reacted with the cyclic sulfone (II) will yield a small amount of the monomer (IV), Xue does not provide enough information for one of skill in the art to determine how to alter the reaction to achieve the much higher yields which are required for practical implementation, generally at least about 50%, typically at least ca. 90%. It is found in a preferred embodiment of the present invention, that $CF_3SO_2NNa_2$ in purified form is highly effective in producing the monomeric composition (IV) with, surprisingly, virtually no side reaction, to provide yields of 50 mol-%, especially yields of 90 mol-%, most especially yields of 95 mol-% or greater. The yield of the desired monomer (IV) depends strongly on the concentration of the $CF_3SO_2NNa_2$ in the starting composition.

In the process of the invention, the dimetal sulfonyl amide salt starting material $(RSO_2NM_b)_{3-b}M'_c$, (V), should, preferably, first itself be produced at high yield. In (V), R is aryl, fluoro-aryl, or $XCF_2$- where X is H, halogen, fluorinated or non-fluorinated linear alkyl radicals having 1–10 carbons or cyclic alkyl radicals having 3–10 carbons, optionally substituted by one or more ether oxygens, M' is an alkaline earth metal, b=1 or 2, c=0 or 1, M is alkaline earth or alkali metal when b is 1 or 2 respectively and c=0, and M is alkali metal when b=1 and c=1, with the proviso that c≠1 when b=2.

Preferably, M is an alkali metal and c=0, b=2, and R is a perfluoroalkyl radical. Most preferably M is sodium and R is a trifluoromethyl radical.

The dimetal sulfonyl amide salt (V) can be made at a purity of greater than 50%, preferably greater than 90%, most preferably greater than 95%, by contacting a sulfonyl amide or monometal sulfonyl amide salt thereof having the formula $(RSO_2NH)_{3-a}M''_a$(VI), with at least one alkali or alkaline earth metal hydride and an aprotic liquid to form a reaction mixture which is permitted to react to any desired degree of conversion up to 100%, which is preferred. In the sulfonyl amide or monometal salt thereof (II), a=1 or 2, M'' is alkaline earth metal when a=1, M'' is alkali metal or hydrogen when a=2, and R is aryl, fluoro-aryl, or $XCF_2$- where X is H, halogen, or a fluorinated or non-fluorinated linear alkyl radical having 1–10 carbons or cyclic alkyl radicals having 3–10 carbons, optionally substituted by one or more ether oxygens. The hydride may consist of a mixture of more than one alkali or alkaline earth hydrides, or a mixture of alkali and alkaline earth hydrides. If preferred, the reaction may proceed in stages with different hydrides being fed to the reaction at different times.

Preferably R is perfluoroalkyl, most preferably trifluoromethyl, and M'' is preferably sodium. $CF_3SO_2NH_2$ is the preferred starting material for preparing the preferred $CF_3SO_2NNa_2$ employed in the present process. The preferred aprotic liquid is acetonitrile. Preferably, the reaction to produce the $CF_3SO_2NNa_2$ is continued until one or the other starting material is completely consumed and reaction stops. More preferably the stoichiometry is adjusted so that only trace amounts of either starting material remain when reaction is complete. Most preferably, the hydride is added at slightly below stoichiometric quantity.

A particularly surprising aspect of the present invention is that the highly purified form of the dimetal sulfonyl amide salt (V) is reacted with the cyclic sulfone (II) to form the desired monomeric composition (IV) in yields approaching 100% with virtually no side reactions.

The sulfonyl amide and monometal salt thereof (VI) are soluble in the aprotic solvents employed in the process of preparing the dimetal sulfonyl amide salt (V), but the dimetal sulfonyl amide salt (V) itself is not. The surprising insolubility of the dimetal sulfonyl amide salt (V) in aprotic solvents is not taught or suggested in the art. The solubility difference is exploited to separate the reaction product from the reaction mixture and obtain a composition comprising sulfonyl amide salts at least 50 mol-%, preferably at least 90 mol-%, most preferably at least 95 mol-%, of which salts are represented by the formula $(RSO_2NM_b)_{3-b}M'$, (V), as hereinabove defined. Any convenient method known in the art for separating solids from liquids may be employed, including filtration, centrifugation and, distillation.

While it is preferred to permit the reaction to run to completion, this may not always be practical depending upon the aprotic solvent chosen. In neat acetonitrile, 100% conversion is achieved in about 4 hours, at room temperature. However, in neat THF, six days of reaction is required for 100% conversion. In the latter case, it may be desired to separate the reaction product before the reactants have fully reacted. The method of separation based upon the heretofore unknown solubility difference, described above provides a practical method for isolating the sulfonyl amide salt (V) at high purity when conversion has been low.

Residual hydride left over from the synthesis of the sulfonyl amide salt (V) is not highly deleterious to the efficacy of the process of the present invention. While not critical, the $CF_3SO_2NNa_2$ preferred for the process of the present invention is substantially free of contamination by NaH. This is achieved by employing slightly less than the stoichiometric amount of NaH in its preparation, thereby insuring that when the reaction achieves full conversion, the NaH will be exhausted. Any excess of the soluble intermediate $CF_3SO_2NHNa$ is easily separated by washing/filtration cycles, preferably using fresh aliquots of solvent.

In preparation the dimetal sulfonyl amide salt, (V) it has been found that the components of the reaction mixture may be combined in any order, but that it is preferred to first mix the sulfonyl amide or a monometal salt thereof (II), with the aprotic liquid to form a solution, following with addition of the hydride after the solution has formed. First mixing the hydride with the aprotic solvent has resulted in poor reaction or slower than expected conversion.

A suitable temperature for preparing the dimetal sulfonyl amide salt (V) will lie between the melting point and the boiling point of the aprotic liquid selected. It has been found to be satisfactory to conduct the process of the invention at room temperature. However, somewhat higher temperatures result in faster reaction. In the most preferred embodiment of the invention, acetonitrile is employed as the solvent at a temperature between about 0° C. and 80° C., preferably between room temperature and 80° C., most preferably between room temperature and 60° C.

Aprotic solvents suitable for preparing the dimetal sulfonyl amide salt (V) starting material should be substantially free of water. Water causes the reaction to reverse, for example to form $CF_3SO_2NHNa$ and NaOH, and provides a route for making a sulfonate instead of an imide. In a preferred embodiment, it has been found satisfactory to employ acetonitrile having water content less than or equal to about 500 PPM, with water content less than or equal to ca. 50 PPM more preferred. Acetonitrile is quite hygroscopic, and care should be taken in handling to avoid water contamination from the atmosphere.

The preferred aprotic solvent for the preparation of the dimetal sulfonyl amide salt (V) is acetonitrile. Acetonitrile has been found to accelerate the conversion by a considerable amount over other aprotic solvents. In neat acetonitrile, essentially quantitative conversion is achieved in about 4 hours. In the presence of as little as 5% acetonitrile in THF, essentially quantitative conversion is achieved in about 25 h. These results contrast starkly with the six days required under the conditions taught by Xue.

Solvent selection has a large effect on the rate of conversion, thought most aprotic solvents will lead to high conversion over sufficient time. Acetonitrile is highly preferred. Other aliphatic and aromatic nitriles, while suitable, do not appear to be particularly better than the THF employed by Xue but may be employed as substitutes for THF. Suitable nitriles include higher alkyl nitriles, dinitriles such as addiponitrile, benzonitrile, and the like. Other suitable solvents include ethers, DMF, DMSO, DMAC, and amides. Combinations of solvent are also useful.

Any of the methods hereinabove, alone or in combination, provide a highly purified form of the dimetal sufonyl amide salt (V). The highly purified form of the dimetal sulfonyl amide salt $(RSO_2NM_b)_{3-b}M'$, (V), greater than 95% purity, which is readily achieved using the methods herein described, is then suitable for use in the process of the present invention producing pure monomer (IV) at high yields, the purity of the monomer (IV) depending directly upon the purity of (V) prepared according to the invention. Any of the methods of preparation herein described are capable of providing (V) in purities of greater than 95%.

The atmosphere to which the dimetal sulfonyl amide salt (V) is exposed should be substantially free of water as well. Water vapor concentrations of about 25 ppm have been found to be suitable. Higher levels of water vapor concentration can be tolerated, but it should be understood that the higher the water vapor concentration of the atmosphere, the greater the contamination during subsequent reaction. As a general rule, the less water the better, in whatever form.

The term "inert atmosphere" as used herein refers to an anhydrous atmosphere having a water vapor concentration of less than about 50 ppm. It is not meant to imply a non-oxidative atmosphere. Thus, the reactions herein may be accomplished in desiccated air as well as in dry nitrogen or other non-chemically active gases. Dry nitrogen, however, is preferred.

Preferably, $CF_3SO_2NH_2$ is dissolved at a concentration in the range of 5–10% by weight in acetonitrile in an inert atmosphere such as nitrogen. At higher concentrations good mixing may become more difficult to maintain as the insoluble $CF_3SO_2NNa_2$ product begins to form, creating a dispersion. Therefore, at concentrations higher than about 10% by weight, other forms of agitation may be preferred over simple stirring, such as ultrasonic agitation, or microfluidization such as may be achieved using a MicroFluidizer™ available from Microfluidics, Inc., Newton, Mass.

Maintaining the inert atmosphere, NaH is added with agitation continuing until the reaction is complete in about four hours. Hydrogen gas evolution rate, determined by any convenient method known in the art, has been found to be an effective indicator of reaction. The cessation of hydrogen gas flow signals completion of the reaction.

The amount of NaH added depends upon the particular requirements of the practitioner hereof. Adding a slight excess over the stoichiometric amount of NaH ensures complete conversion of the $CF_3SO_2NH_2$ or $CF_3SO_2NHNa$ to $CF_3SO_2NNa_2$. However, this leaves $CF_3SO_2NNa_2$ so prepared still contaminated with insoluble NaH from which it may be difficult to separate. However, it has been found that residual NaH is largely inert to the cyclic sulfone (II) in the process of the invention and to the product thereof, namely the monomer (IV). On the other hand, if the goal is to achieve the cleanest possible $CF_3SO_2NNa_2$ then a slight deficit of NaH below the stoichiometric amount may be employed to ensure that the NaH will be fully consumed. Employing a deficit of NaH is likely to result in less than complete conversion of the $CF_3SO_2NH_2$ or $CF_3SO_2NHNa$ to $CF_3SO_2NNa_2$. The soluble residual $CF_3SO_2NHNa$ is easily washed away from the insoluble $CF_3SO_2NNa_2$.

The dimetal sulfonyl amide salt (I) may be dried under vacuum at elevated temperature, but the user must be aware of the possibility of spontaneous and violent decomposition of the material. It is highly recommended to never handle this material in a totally dry state. It is highly recommended to keep the material wet at all times. It seems that the smaller composition $CF_3SO_2NNa_2$ is less stable than the compositions of higher molecular weight like $CF_4F_9SO_2NNa_2$. A suitable temperature depends upon the specific composition thereof. The preferred $CF_3SO_2NNa_2$ should be dried at a temperature preferably not higher than 80° C., most preferably not higher than 65° C. Certain of the compositions of the invention, including the preferred $CF_3SO_2NNa_2$, have been observed to undergo certain decomposition aggressively when heated to the decomposition threshold but it has been observed at one occasion that the preferred $CF_3SO_2NNa_2$ undergoes spontaneous and violent decomposition at room temperature. The compound is moisture sensitive and must be handled under anhydrous conditions. It is believed that the product may be somewhat unstable, and potentially subject to explosive decomposition.

In the process of the invention, the dimetal sulfonyl amide salt (V), prepared as hereinabove described, is combined with the cyclic sulfone (II) preferably with agitation to form the desired monomeric composition (IV). Preferably the dimetal sulfonyl amide salt (V) is neat in order to minimize side reactions involving residual starting material. In the cyclic sulfone (II), X is preferably F.

The reaction of the cyclic sulfone and the dimetal sulfonyl amide salt (V) is conducted in an inert atmosphere at a temperature at which the cyclic sulfone is a liquid, in the range of 0° C. to 67° C., preferably, 20° C. to 50° C. Room temperature has been found to provide satisfactory results, although higher reaction rate will be achieved at temperatures above room temperature.

The process of the invention may be conducted in the absence of an inert liquid medium when an excess of cyclic sulfone, which is liquid at room temperature, is provided to ensure sufficient mixing. However, it is preferred to conduct the process of the invention in an added inert liquid medium. Numerous organic liquids are suitable for use as an inert liquid medium for the process of the invention; the requirements are not strict, beyond liquidity and inertness. It is preferred to use a solvent that dissolves the monomer but not the NaF by-product so that it can easily be filtered off. Preferred liquids are ethers, including THF, nitriles, DMSO, amides, and sulfolanes. Ethers are more preferred, with THF most preferred. It is found, surprisingly, that acetonitrile which is preferred for preparing the $CF_3SO_2NNa_2$ starting material, is less preferred for use at an inert liquid medium for conversion of the cyclic sulfone to the monomeric composition. And, conversely, the ethers which are not highly effectual in preparing $CF_3SO_2NNa_2$ are preferred for the process of the present invention for conversion of cyclic sulfone to the monomeric composition.

The reactants are preferably agiated in order to provide high interfacial area for the reaction to take place so as to provide the desired high product yield. While the manner of agitating the reaction mixture is not critical, agitation should maintain the degree of homogeneity in the reaction mixture needed to ensure the desired level of conversion. Suitable means for agitating include, but are not limited to, shaking, stirring, blending, ultrasound, and microfluidization.

Reaction time will vary depending upon the particular reactants involved, the temperature, the liquid medium employed, and concentration of reactants, and the degree of mixing or agitation. It has been found in the preferred embodiment of the invention that reaction times of about 2 hours generally suffice.

The monomeric composition provided by the process of the invention may be copolymerized with fluorinated or non-fluorinated monomers such as tetrafluoroethylene, ethylene trifluoro ethylene, vinylidene fluoride or vinyl fluoride. Termonomers, which may be employed therewith, include hexafluoropropylene, perfluoroalkyl vinyl ethers, ethylene, tetrafluoroethylene, trifluoro ethylene, vinylidene fluoride or vinyl fluoride.

The monomeric composition prepared by the process of the invention may also be converted to a sulfonyl fluoride, copolymerized with, e.g., TFE, then hydrolyzed as appropriate according to the methods taught in Resnick, op.cit..

In a preferred embodiment, the monomeric composition is prepared by reaction of $CF_3SO_2NNa_2$ with the cyclic sulfone (II) wherein X is F, to form the sodium imide form of the monomeric composition (IV). The monomeric composition so-formed is dissolved in THF followed by treatment with LiCl in THF to effect ion exchange to the lithium imide form according to the method of Jüschke et al., Z. Naturforsch., 53b (1998) 135–144.The by-product NaCl is filtered off and the lithium imide monomeric composition is copolymerized with vinylidene fluoride after drying according to the teachings in Feiring et al., WO9945048(A1). Alternatively, and also according to the teachings in Feiring et al., op.cit., the sodium imide monomeric composition may be copolymerized first, afterwards the polymeric composition may be treated with LiCl in THF to accomplish ion exchange. The monomeric or polymeric composition so-formed can also be converted into the acid form following the teachings of DesMarteau, op.cit., by treating the sodium form with sulfuric acid. The acid form can be neutralized with e.g., LiOH to obtain the lithium composition.

EXAMPLES

Example 1

$CF_3SO_2NH_2$ was purchased from Tokyo Chemical Industry, Portland, Oreg. (TCI) and dried and purified by two cycles of sublimation under a vacuum of ca. $10^{-3}$ Torr, employing a water cooled (~20° C.) cold-finger, and a oil bath at 80° C. Anhydrous acetonitrile was purchased from EM Science Gibbstown, N.J., slurried with $P_2O_5$ and distilled to ensure dryness, and stored over molecular sieves inside a dry box until ready to be used. Sodium hydride (95%) was purchased from Aldrich Chemical.

Inside a model HE-63-P dry-box (Vacuum Atmosphere Company, Hawthorne, Calif.) having a dry nitrogen atmosphere, a round bottom flask was charged with 30.003 g of the sublimed $CF_3SO_2NH_2$ and 750 ml of the dried acetonitrile. 9.003 g of the sodium hydride was slowly added over a period of 60 min while the reaction mixture was stirred with a magnetic stir bar. The temperature of the reaction mixture increased from 21.6° C. to 50.5° C. during the addition process. The mixture was stirred at room temperature for 20 h. After about 4–5 hours the reaction medium had taken on an opaque "creamy" appearance, and no further bubbling, indicative of the evolution of hydrogen, was observed.

The reaction mixture was filtered through a glass-filter (medium porosity) inside the dry-box. The white solid was washed three times with 100 ml of the anhydrous acetonitrile, transferred from the filter to a Schlenk flask and dried under vacuum ($10^{-2}$ Torr) at room temperature for 5 h., still in the dry box. Approximately 10% of the filtrate was lost in transferring from the filter to the Schlenk flask. The Schlenk flask was sealed, removed from the dry-box, and subject to further evacuation under oil pump vacuum ($10^{-3}$ Torr) for 15 h at room temperature. The Schlenk flask was then immersed in an oil bath set at 50° C. and held for four hours at which time the bath was heated to 65° C. and the Schlenk flask was held therein for an additional 20 h while still subject to evacuation under oil pump vacuum ($10^{-3}$ Torr). Afterwards, the $CF_3SO_2NNa_2$ was only handled inside the dry-box.

30.0 grams of product were isolated. The product decomposed at 110° C. while generating large amounts of a gas.

It has been observed at one occasion that the preferred $CF_3SO_2NNa_2$ undergoes spontaneous and violent decomposition at room temperature and it is therefore recommended to not dry this material but instead to keep it as a suspension at all times.

Example 2

Inside the dry box of Example 1, a flask was charged with 5.142 g $C_4F_9SO_2NH_2$ made from $C_4F_9SO_2F$ and $NH_3$ according to the method of Meußdoerffer et al, op.cit., and 100 ml of anhydrous acetonitrile prepared as in Example 1. 0.784 g NaH (Alrich) was slowly added over a period of 5 min. The mixture was stirred at room temperature for 24 h without observation. Insoluble $C_4F_9SO_2NNa_2$ had precipitated at the bottom of the flask. The reaction mixture was filtered through a glass filter (fine porosity) and the white residue was washed three times with 50 ml of anhydrous acetonitrile. The residue was collected from the filter and placed in a Schlenk-flask. Afterwards, the material was brought outside the dry-box and dried under oil pump vacuum ($10^{-3}$ Torr) for 24 h at an oil bath temperature of 65° C. $C_4F_9SO_2NNa_2$ was only handled inside the dry-box. 4.37 g of product were isolated.

It has been observed at one occasion that the preferred $CF_3SO_2NNa_2$ undergoes spontaneous and violent decomposition at room temperature and it is therefore recommended to not dry this material but instead to keep it as a suspension at all times.

Example 3

Employing the reagents and equipment of Example 1, inside the dry-box 3.123 g of sublimed $CF_3SO_2NH_2$ was dissolved in 100 ml of the anhydrous acetonitrile in a round-bottom flask. 1.127 g of the sodium hydride was slowly added to form a first reaction mixture. Addition of NaH took place over a period of 10 min while the first reaction mixture was stirred with a magnetic stirring bar at room temperature. After 3 h, no fluorine could be detected by $^{19}F$ NMR in the solution indicating complete conversion of $CF_3SO_2NH_2$ to $CF_3SO_2NNa_2$, thereby forming a mixture of $CF_3SO_2NNa_2$ and acetonitrile, with some residual NaH.

Example 4

Inside the dry-box of Example 1, a round bottom flask was charged with 5.027 g of the $C_4F_9SO_2NH_2$ made from $C_4F_9SO_2F$ and $NH_3$ according to the method of Meußdoerffer et al, op.cit., and 100 ml of anhydrous acetonitrile prepared as in Example 1. 0.890 g of sodium hydride (Aldrich) was slowly added to form a first reaction mixture. Addition of NaH took place over a period of 10 min while the reaction mixture was stirred at room temperature with a magnetic stir bar. After 22 h of stirring, no fluorine could be detected by $^{19}F$ NMR in the solution indicating complete conversion, thereby forming a mixture of $C_4F_9SO_2NNa_2$ in acetonitrile, contaminated by some residual NaH.

Example 5

Inside the dry-box, a round bottom flask was charged with 3.051 g, of the $CF_3SO_2NH_2$ made in the manner of Example 1 and 100 ml of anhydrous acetonitrile prepared as in Example 1. 1.068 g of the NaH (Aldrich) was added slowly over a period of 5 min. The mixture was stirred at room temperature for 26 h inside the dry-box and checked periodically by fluorine NMR until no fluorine could be detected.

Example 6

As in Example 1, a round bottom flask was charged with 3.082 g of the $CF_3SO_2NH_2$ prepared as in Example 1 and 100 ml of anhydrous acetonitrile prepared as in Example 1. 1.134 g of the NaH (Aldrich) was added slowly over a period of 5 min. The mixture was stirred at room temperature for 16 h inside the dry-box. No fluorine could be detected by NMR.

Example 7

THF received from Aldrich was refluxed and distilled from sodium metal to provide anhydrous THF. As in Example, 1, 0.646 g of the $CF_3SO_2NNa_2$ prepared in Example 1 was suspended in a 50 ml of the thus prepared anhydrous THF. The cyclic sulfone

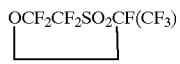

was purchased from the Shanghai Institute of Organic chemistry. The material as received underwent multiple spinning band distillations, and was condensed from $P_2O_5$. 0.900 g of the thus treated cyclic sulfone was added at room temperature while stirring the suspension with a magnetic stir bar. The reaction mixture turned clear indicating complete reaction of the $CF_3SO_2NNa_2$ and a fine powder started to precipitate indicative of the NaF by-product. After 30 min., $^{19}$F NMR in $d^8$-THF confirmed the structure $CF_2=CFOCF_2CF_2SO_2N(Na)SO_2CF_3$.

The reaction mixture was centrifuged for 20 min and then decanted through a glass filter with medium porosity. All volatiles were removed under vacuum and the slightly yellow residue was dried at 100° C. at $10^{-3}$ Torr oil pump vacuum for 24 h. Yield was 1.057 g. $^{19}$F NMR $d^8$-THF ($CF_2^{AA'}=CF^BOCF_2^CCF_2SO_2N(Na)SO_2CF_3^E$):-82.6 ppm (E, 3F),-86.0 ppm (C, 2F),-118.2 ppm,-125.5 ppm (A, 1F, A', 1F),-119.7 ppm (D, 2F),-138.0 ppm (B, 1F).

Example 8

Inside the dry-box of Example 1, 1.200 g of the $C_4F_9SO_2NNa_2$ of Example 2 was suspended in 50 ml of the THF of Example 7. 0.981 g of the cyclic sulfone of Example 7 was added at room temperature while stirring the suspension with a magnetic stirring bar. The reaction mixture turned clear during the next few hours and a fine powder started to precipitate. $^{19}$F NMR in $d^8$-THF taken after 120 min showed the formation of $CF_2=CFOCF_2CF_2SO_2N(Na)SO_2CF_2CF_2CF_2CF_3$ The reaction mixture was centrifuged for 20 min and then decanted through a glass filter with medium porosity. All volatiles were removed under vacuum and the slightly yellow residue was dried at 100° C. at $10^{-3}$ Torr oil pump vacuum for 24 h. The yield was 1.685 g of $CF_2=CFOCF_2CF_2SO_2N(Na)SO_2CF_2CF_2CF_2CF_3$ $^{19}$F NMR in $CD_3CN$ ($CF_2^{AA'}=CF^BOCF_2^CCF_2^DSO_2N(Na)SO_2CF_2^ECF_2^FCF_2^GCF_3^H$):-80.4 ppm (H, 3F),-82.4 ppm (C, 2F),-112.7 ppm (E, 2F),-113.6 ppm,-121.6 ppm (A, 1F, A', 1F),-115.9 ppm (D, 2F),-120.4 ppm (F, 2F),-125.2 ppm (G, 2F),-134.7 ppm (B, 1F).

Comparative Example 1

Inside the dry-box of Example 1, a flask was charged with 0.93 g of $CF_3SO_2NHNa$ prepared by treating $CF_3CO_2NH_2$ with NaOH, 0.135 g NaH (Aldrich) and 20 ml of anhydrous THF (Aldrich, distilled off Na metal). The reaction mixture was stirred for 4 h at room temperature and was then filtered through a glass filter (fine porosity). The filtrate was collected in a flask and brought outside the dry-box. All solvents were removed under vacuum ($10^{-3}$ Torr) and the residue was heated to 65° C. for 24 h at $10^{-3}$ Torr. 0.862 g (5.04 mmol) of $CF_3SO_2NHNa$ were recovered, corresponding to 92.6% of the starting material. The dried material was brought into the dry-box and 50 ml of anhydrous acetonitrile were added because it is suspected that $CF_3SO_2NNa_2$ is slightly soluble in THF. The majority of the material was dissolved in the acetonitrile and only a slight trace of a solid could be observed in the solution. It was not attempted to separate this residue. It should be safe to assume that less than 10% of the $CF_3SO_2NHNa$ have been converted to $CF_3SO_{NNa2}$ after 4 h in THF at room temperature.

Comarative Example 2

Following the procedures of Comparative Example 1, inside the dry-box, the round bottom flask was charged with 0.866 g of the $CF_3SO_2NHNa$ of Comparative Example 1. The material was dissolved in 100 m of anhydrous THF (Aldrich; distilled from Na metal; stored over molecular sieves inside the dry-box). 0.171 g of NaH was placed in the SRAD. After the required connections were made to a gas collection tube, the reaction mixture was stirred at room temperature and the NaH was added to the solution. No obvious reaction could be observed. A total of 113.3 ml of collected hydrogen would represent complete conversion under normalized conditions. The gas collected as a function of time is shown in Table 1.

TABLE 1

| Elapsed time (after addition of NaH) | Gas Collected (ml) | estimated % conversion |
| --- | --- | --- |
| 0 h 45 min | 4 | 3.5 |
| 2 h 30 min | 10 | 8.8 |
| 5 h 45 min | 10 | 8.8 |
| 21 h 45 min | 18 | 15.9 |
| 26 h 15 min | 25 | 22.1 |
| 32 h 45 min | 28 | 24.7 |
| 47 h | 38 | 33.6 |
| 49 h 15 min | 43 | 38.0 |
| 53 h 30 min | 47 | 41.6 |
| 84 h 45 min | 53 | 46.9 |
| 86 h 45 min | 55 | 48.6 |
| 97 h 15 min | 65 | 57.5 |
| 118 h | 78 | 69.0 |
| 122 h 15 min | 85 | 75.2 |
| 139 h 45 min | 110 | 97.3 |
| 142 h | 114 | 100.5 |

The reaction was completed after six days at room temperature. The reaction flask was brought inside the dry-box.

PSEPVE (2.511 g; 5.63 mmol; DuPont) was added to the colorless reaction mixture that contained a white solid. After 10 min stirring at room temperature, the reaction mixture turned clear. A fine precipitation formed. An NMR sample was collected after 1 h showing the formation of the product $CF_2=CFOCF_2CF(CF_3)OCF_2CF_2SO_2N(Na)SO_2CF_3$ and excess PSEPVE.

What is claimed is:

1. A process for forming at a yield greater than 50 mol-% a monomeric composition represented by the formula

where X is F or perfluoroalkyl having 1–4 carbons optionally substituted by ether oxygen, M is an alkali or alkaline earth metal when "y" is respectively 1 or 2, R is aryl, fluoro-aryl, or $XCF_2$-where X is H, halogen, fluorinated or non-fluorinated linear alkyl having 1–10 carbons or cyclic alkyl having 3–10 carbons, optionally substituted by one or more ether oxygens; the process comprising:

contacting in an inert atmosphere a cyclic sulfone represented by the structure

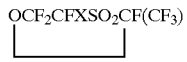

wherein X is F or perfluoroalkyl having 1–4 carbons optionally substituted by ether oxygen with a composition comprising sulfonyl amide salts of which said salts at least 50 mol-% are dimetal sulfonyl amide salts represented by the formula $(RSO_2NM_b)_{3-b}M'_c$, wherein R is aryl, fluoro-aryl, or $XCF_2$-where X is H, halogen, fluorinated or non-fluorinated linear alkyl radicals having 1–10 carbons or cyclic alkyl radicals having 3–10 carbons, optionally substituted by one or more ether oxygens, M' is an alkaline earth metal, b=1 or 2, c=0 or 1, M is alkaline earth or alkali metal when b is 1 or 2 respectively and c=0, and M is alkali metal when b=1 and c=1, with the proviso that c≠1 when b=2, thereby forming a ring-opening reaction mixture;

reacting said ring-opening reaction mixture at a temperature in the range of 0 to 67° C.

2. The process of claim 1 wherein M is an alkali metal and c=0.

3. The process of claim 1 wherein R is a fluoroalkyl radical having 1–4 carbons optionally substituted by ether oxygen.

4. The process of claim 1 wherein R is a trifluoromethyl.

5. The process of claim 1 wherein X is F.

6. The process of claim 1 wherein at least 90 mol-% of said salts are sulfonyl amide salts represented by the formula $(RSO_2NM_b)_{3-b}M'_c$.

7. The process of claim 1 wherein at least 90 mol-% of said cyclic sulfone has been converted to said monomeric composition.

8. The process of claim 1 further comprising an inert liquid medium in which said ring-opening reaction mixture is formed and reacted.

9. The process of claim 8 wherein said inert liquid medium is selected from the group consisting of ethers, nitriles, dimethylsulfoxide, amides, and sulfolanes.

10. The process of claim 9 wherein said inert liquid medium is tetrahydrofuran.

11. The process of claim 1 further comprising a process for preparing said composition comprising sulfonyl amide salts the process comprising:

in an inert atmosphere at least one alkali or alkaline earth hydride, a sulfonyl amide or monometal sulfonyl amide salt thereof having the formula

wherein a=1 or 2, M" is alkaline earth metal when a=1, M" is alkali metal hydrogen when a=2, and R is aryl, fluoro-aryl, or $ZCF_2$-where Z is H, halogen, or a fluorinated or non-fluorinated linear alkyl radical having 1–10 carbons or cyclic alkyl radicals having 3–10 carbons, optionally substituted by one or more ether oxygens; and, at least one aprotic liquid, thereby forming an anterior reaction mixture; and, said anterior reaction mixture to achieve conversion of said $(RSO_2NH)_{3-a}M"$ to said $(RSO_2NM_b)_{3-b}M'_c$ of claim 1.

12. The process of claim 11 wherein the aprotic liquid comprises acetonitrile.

13. The process of claim 11 wherein the hydride is an alkali metal hydride.

14. The process of claim 13 wherein the hydride is sodium hydride.

15. The process of claim 11 wherein M" is hydrogen.

16. The process of claim 11 wherein R is a perfluoroalkyl radical having 2–4 optionally substituted by ether oxygen.

17. The process of claim 11 wherein R is a trifluoromethyl radical.

18. The process of claim 11 wherein M is an alkali metal and c=0.

19. The process of claim 11 wherein X is F.

20. The process of claim 11 wherein the cyclic sulfone is contacted with a composition comprising sulfonyl amide salts of which said salts at least 90 mol-% are sulfonyl amide salts represented by the formula $(RSO_2NM_b)_{3-b}M'_c$ of claim 1.

21. The process of claim 11 further comprising an inert liquid medium in which said ring-opening reaction mixture is formed and reacted.

22. The process of claim 11 wherein said inert liquid medium is tetrahydrofuran.

23. The process of claim 22 wherein said inert liquid medium is selected from the group consisting of ethers, nitriles, dimethylsulfoxide, amides, and sulfolanes.

* * * * *